(12) United States Patent
Günther et al.

(10) Patent No.: US 11,684,589 B2
(45) Date of Patent: Jun. 27, 2023

(54) PHARMACEUTICAL COMPOSITIONS FOR USE IN THE THERAPY OF BLEPHARITIS

(71) Applicant: NOVALIQ GMBH, Heidelberg (DE)

(72) Inventors: Bernhard Günther, Dossenheim (DE); Frank Löscher, Schriesheim (DE); Sonja Krösser, Heidelberg (DE)

(73) Assignee: NOVALIQ GMBH, Heidelberg (DE)

( * ) Notice: Subject to any disclaimer, the term of this patent is extended or adjusted under 35 U.S.C. 154(b) by 33 days.

(21) Appl. No.: 16/336,018

(22) PCT Filed: Sep. 20, 2017

(86) PCT No.: PCT/EP2017/073697
§ 371 (c)(1),
(2) Date: Mar. 22, 2019

(87) PCT Pub. No.: WO2018/054932
PCT Pub. Date: Mar. 29, 2018

(65) Prior Publication Data
US 2019/0274970 A1 Sep. 12, 2019

(30) Foreign Application Priority Data

Sep. 22, 2016 (EP) .................................. 16190138

(51) Int. Cl.
*A61K 31/02* (2006.01)
*A61K 9/00* (2006.01)
(52) U.S. Cl.
CPC ............ *A61K 31/02* (2013.01); *A61K 9/0014* (2013.01); *A61K 9/0048* (2013.01)
(58) Field of Classification Search
CPC ..... A61K 31/02; A61K 9/0048; A61K 9/0014
See application file for complete search history.

(56) References Cited

U.S. PATENT DOCUMENTS

| | | | |
|---|---|---|---|
| 2,616,927 A | 11/1952 | Kauck et al. |
| 5,077,036 A | 12/1991 | Long, Jr. |
| 5,326,566 A | 7/1994 | Parab |
| 5,336,175 A | 8/1994 | Mames |
| 5,370,313 A | 12/1994 | Beard |
| 5,518,731 A | 5/1996 | Meadows |
| 5,667,809 A | 9/1997 | Trevino |
| 5,874,469 A | 2/1999 | Maniar et al. |
| 5,874,481 A | 2/1999 | Weers |
| 5,980,936 A | 11/1999 | Krafft et al. |
| 5,981,607 A | 11/1999 | Ding |
| 6,042,845 A | 3/2000 | Sun et al. |
| 6,060,085 A | 5/2000 | Osborne |
| 6,113,919 A | 9/2000 | Cronelus |
| 6,159,977 A | 12/2000 | Reeves |
| 6,177,477 B1 | 1/2001 | George et al. |
| 6,197,323 B1 | 3/2001 | Georgieff |
| 6,224,887 B1 | 5/2001 | Samour et al. |
| 6,262,126 B1 | 7/2001 | Meinert |
| 6,294,563 B1 | 9/2001 | Garst |
| 6,335,335 B2 | 1/2002 | Higashiyama |
| 6,372,243 B2 | 4/2002 | Kobuch et al. |
| 6,391,879 B1 | 5/2002 | Reeves |
| 6,458,376 B1 | 10/2002 | Meadows |
| 6,486,212 B2 | 11/2002 | Meinert |
| 6,489,367 B1 | 12/2002 | Meinert |
| 6,730,328 B2 | 5/2004 | Maskiewicz |
| 7,001,607 B1 | 2/2006 | Menz |
| 7,026,359 B1 | 4/2006 | Gross |
| 7,258,869 B1 | 8/2007 | Berry |
| 7,740,875 B2 | 6/2010 | Dechow |
| 8,029,977 B2 | 10/2011 | Meinert et al. |
| 8,470,873 B2 | 6/2013 | Chen |
| 8,614,178 B2 | 12/2013 | Theisinger et al. |
| 8,796,340 B2 | 8/2014 | Theisinger et al. |
| 8,916,157 B2 | 12/2014 | Krause et al. |
| 8,986,738 B2 | 3/2015 | Meinert |
| 9,241,900 B2 | 1/2016 | Wilson |
| 9,308,262 B2 | 4/2016 | Wilson |
| 9,757,459 B2 | 9/2017 | Theisinger et al. |
| 9,757,460 B2 | 9/2017 | Günther et al. |
| 9,770,508 B2 | 9/2017 | Günther et al. |
| 9,968,678 B2 | 5/2018 | Theisinger et al. |
| 10,045,996 B2 | 8/2018 | Theisinger et al. |
| 10,058,615 B2 | 8/2018 | Günther et al. |
| 10,064,944 B2 | 9/2018 | Wilson |
| 10,123,904 B2 | 11/2018 | Chauhan et al. |
| 10,369,117 B2 | 8/2019 | Günther et al. |
| 10,449,164 B2 | 10/2019 | Günther et al. |
| 10,507,132 B2 | 12/2019 | Graf et al. |
| 10,525,062 B2 | 1/2020 | Theisinger et al. |
| 10,555,953 B2 | 2/2020 | Theisinger et al. |
| 10,576,154 B2 | 3/2020 | Günther et al. |
| 10,682,315 B2 | 6/2020 | Scherer et al. |
| 10,813,976 B2 | 10/2020 | Löscher et al. |
| 11,154,513 B2 | 10/2021 | Scherer et al. |
| 11,160,865 B2 | 11/2021 | Theisinger et al. |
| 11,273,174 B2 | 3/2022 | Löscher et al. |

(Continued)

FOREIGN PATENT DOCUMENTS

| | | |
|---|---|---|
| EP | 0 089 815 | 9/1983 |
| EP | 0 670 159 | 9/1995 |
| EP | 0 965 329 | 12/1999 |
| EP | 0 965 334 | 12/1999 |
| EP | 1 152 749 | 11/2001 |

(Continued)

OTHER PUBLICATIONS

Ahmed, et al., "Disposition of Timolol and Inulin in the Rabbit Eye Following Corneal Versus Non-Corneal Absorption," International Journal of Pharmaceutics, 1987, 38:9-21.

(Continued)

*Primary Examiner* — Shobha Kantamneni
(74) *Attorney, Agent, or Firm* — Hoxie & Associates LLC

(57) ABSTRACT

The present invention provides a pharmaceutical composition comprising 1-perfluorohexyl-octane (F6H8) for use in the therapy, treatment, prevention or amelioration of anterior or posterior blepharitis, preferably posterior blepharitis or symptoms associated therewith. Furthermore, the present invention provides a pharmaceutical kit for the therapy of anterior or posterior blepharitis or symptoms associated therewith.

12 Claims, No Drawings

(56) References Cited

U.S. PATENT DOCUMENTS

| | | |
|---|---|---|
| 2002/0004063 A1 | 1/2002 | Zhang |
| 2002/0128527 A1 | 9/2002 | Meinert |
| 2003/0018044 A1 | 1/2003 | Peyman |
| 2003/0027833 A1 | 2/2003 | Cleary et al. |
| 2003/0170194 A1 | 11/2003 | Piotrowiak |
| 2004/0044045 A1 | 3/2004 | Burk |
| 2004/0082660 A1 | 4/2004 | Ueno |
| 2004/0265362 A1 | 12/2004 | Susilo |
| 2004/0266702 A1 | 12/2004 | Dawson |
| 2005/0075407 A1 | 4/2005 | Tamarkin et al. |
| 2005/0079210 A1 | 4/2005 | Gupta |
| 2005/0175541 A1 | 8/2005 | Lanza et al. |
| 2005/0274744 A1 | 12/2005 | Spada et al. |
| 2005/0288196 A1 | 12/2005 | Horn |
| 2006/0009522 A1 | 1/2006 | Dana et al. |
| 2006/0153905 A1 | 7/2006 | Carrara et al. |
| 2008/0050335 A1 | 2/2008 | Faour et al. |
| 2008/0153909 A1 | 6/2008 | Dana et al. |
| 2008/0207537 A1 | 8/2008 | Turner et al. |
| 2008/0260656 A1 | 10/2008 | Mallard |
| 2009/0149546 A1 | 6/2009 | Chang |
| 2010/0006600 A1 | 1/2010 | Dascanio |
| 2010/0008996 A1 | 1/2010 | Meinert |
| 2010/0016814 A1 | 1/2010 | Gokhale et al. |
| 2010/0226997 A1 | 9/2010 | Bowman et al. |
| 2010/0274215 A1 | 10/2010 | Wong et al. |
| 2011/0269704 A1 | 11/2011 | Seigfried |
| 2012/0010280 A1 | 1/2012 | Aleo et al. |
| 2012/0095097 A1 | 4/2012 | Tabuchi et al. |
| 2012/0238639 A1 | 9/2012 | Theisinger et al. |
| 2013/0046014 A1 | 2/2013 | Theisinger et al. |
| 2013/0084250 A1 | 4/2013 | Hagedorn et al. |
| 2013/0266652 A1 | 10/2013 | Theisinger et al. |
| 2013/0303473 A1 | 11/2013 | Wilson |
| 2013/0336557 A1 | 12/2013 | Cruzat et al. |
| 2014/0004197 A1 | 1/2014 | Theisinger et al. |
| 2014/0100180 A1 | 4/2014 | Günther et al. |
| 2014/0140942 A1 | 5/2014 | Günther et al. |
| 2014/0369993 A1 | 12/2014 | Günther et al. |
| 2015/0224064 A1 | 8/2015 | Günther et al. |
| 2015/0238605 A1 | 8/2015 | Günther et al. |
| 2016/0101178 A1 | 4/2016 | Wilson |
| 2016/0159902 A1 | 6/2016 | Günther et al. |
| 2016/0243189 A1 | 8/2016 | Gu et al. |
| 2017/0020726 A1 | 1/2017 | Labombarbe et al. |
| 2017/0087100 A1 | 3/2017 | Scherer et al. |
| 2017/0087101 A1 | 3/2017 | Scherer et al. |
| 2017/0182060 A1 | 6/2017 | Wiedersberg et al. |
| 2017/0348285 A1 | 12/2017 | Hellstron |
| 2018/0360908 A1 | 12/2018 | Beier et al. |
| 2019/0328717 A1 | 10/2019 | Günther et al. |
| 2019/0343793 A1 | 11/2019 | Günther et al. |
| 2020/0060987 A1 | 2/2020 | Günther et al. |
| 2020/0129543 A1 | 4/2020 | Löscher et al. |
| 2020/0188318 A1 | 6/2020 | Günther et al. |
| 2020/0206241 A1 | 7/2020 | Theisinger et al. |
| 2020/0246463 A1 | 8/2020 | Günther et al. |
| 2020/0268648 A1 | 8/2020 | Günther et al. |
| 2020/0268682 A1 | 8/2020 | Günther et al. |
| 2020/0338015 A1 | 10/2020 | Scherer et al. |
| 2021/0023166 A1 | 1/2021 | Löscher et al. |
| 2021/0069014 A1 | 3/2021 | Löscher et al. |
| 2021/0106558 A1 | 4/2021 | Löscher et al. |
| 2021/0121471 A1 | 4/2021 | Löscher et al. |
| 2021/0228595 A1 | 7/2021 | Löscher et al. |
| 2021/0236591 A1 | 8/2021 | Leo et al. |
| 2021/0315832 A1 | 10/2021 | Scherer et al. |
| 2021/0346313 A1 | 11/2021 | Beier et al. |
| 2022/0008397 A1 | 1/2022 | Xu et al. |
| 2022/0031844 A1 | 2/2022 | Mauden et al. |
| 2022/0079925 A1 | 3/2022 | Günther et al. |
| 2022/0226426 A1 | 7/2022 | Löscher et al. |

FOREIGN PATENT DOCUMENTS

| | | |
|---|---|---|
| EP | 0 939 655 | 6/2002 |
| EP | 2 110 126 | 10/2009 |
| EP | 2 332 525 | 6/2011 |
| EP | 2 335 735 | 6/2011 |
| EP | 2 462 921 | 6/2012 |
| JP | S6452722 | 2/1989 |
| JP | 2000511157 | 8/2000 |
| JP | 2001/158734 | 6/2001 |
| JP | 2008/505177 | 2/2008 |
| JP | 2011/006348 | 1/2011 |
| WO | WO 1995/033447 | 12/1995 |
| WO | WO 96/40052 | 12/1996 |
| WO | WO 97/12852 | 4/1997 |
| WO | WO 1998/005301 | 12/1998 |
| WO | WO 00/10531 | 3/2000 |
| WO | WO 00/024376 | 5/2000 |
| WO | WO 00/054588 | 9/2000 |
| WO | WO 2002/49631 A1 | 6/2002 |
| WO | WO 2005/018530 | 3/2005 |
| WO | WO 2005/099718 | 10/2005 |
| WO | WO 2005/099752 | 10/2005 |
| WO | WO 2005/123035 | 12/2005 |
| WO | WO 2006/007510 | 1/2006 |
| WO | WO 2006/042059 | 4/2006 |
| WO | WO 2006/048242 | 5/2006 |
| WO | WO 2007/052288 | 5/2007 |
| WO | WO 2008/060359 | 5/2008 |
| WO | WO 2009/013435 | 1/2009 |
| WO | WO 2010/062394 | 6/2010 |
| WO | WO 2010/146536 | 12/2010 |
| WO | WO 2011/009436 | 1/2011 |
| WO | WO 2011/073134 | 6/2011 |
| WO | WO 2011/113855 | 9/2011 |
| WO | WO 2012/052418 | 4/2012 |
| WO | WO 2012/062834 | 5/2012 |
| WO | WO 2012/093113 | 7/2012 |
| WO | WO 2012/121754 | 9/2012 |
| WO | WO 2012/160179 | 11/2012 |
| WO | WO 2012/160180 | 11/2012 |
| WO | WO 2013/110621 | 8/2013 |
| WO | WO 2014/041055 | 3/2014 |
| WO | WO 2014/041071 | 3/2014 |
| WO | WO 2014/154531 | 10/2014 |
| WO | WO 2015/011199 | 1/2015 |
| WO | WO 2018/055101 | 4/2018 |
| WO | WO 2018/115097 | 6/2018 |

OTHER PUBLICATIONS

Baerdemaeker, "Pharmacokinetics in Obese Patients," Continuing Education in Anesthesia, Critical Care & Pain, 2004, 4:152-155.

Barata-Vallejo et al., "(Me$_3$Si)$_3$SiH-Mediated Intermolecular Radical Perfluoroalkylation Reactions of Olefins in Water," J. Org. Chem., 2010, 75:6141-6148.

Bardin et al., "Long-Range Nanometer-Scale Organization of Semifluorinated Alkane Monolayers at the Air/Water Interface," Langmuir, 2011, 27:13497-13505.

Blackie et al., "MGD: Getting to the Root Cause of Dry Eye," Review of Optometry, 2012, pp. 1-12.

Broniatowski, M. et al., "Langmuir Monolayers Characteristics of (Perfluorodecyl)-Alkanes," Journal of Physical Chemistry B, 2004, 108:13403-13411.

Chemical Book, 5-Fluorouracil, available at <http://www.chemicalbook.com/ChemicalProductProperty_EN_CB8162744.htm>, accessed Mar. 7, 2014, 1 page.

Chhadva et al., "Meibomian Gland Disease The Role of Gland Dysfunction in Drye Eye Disease," Ophthalmology (2017) 124(11 Supplement): S20-S26.

Costa Gomes et al., "Solubility of dioxygen in seven fluorinated liquids," Journal of Fluorine Chemistry, 2004, 125:1325-1329.

Davies, "Biopharmaceutical Considerations in Topical Ocular Drug Delivery," Clin. Exper. Pharmacol. Physiol., 2000, 27:558-562.

Dembinski et al., Semi-fluorinated Alkanes as Carriers for Drug Targeting in Acute Respiratory Failure, Experimental Lung Research, 2010, 36(8):499-507.

(56) References Cited

OTHER PUBLICATIONS

Dias et al., "Solubility of oxygen in liquid perfluorocarbons," Fluid Phase Equilibria, 2004, 222-223:325-330.
Dutescu et al., "Semifluorinated alkanes as a liquid drug carrier system for topical ocular drug delivery," European Journal of Pharmaceutics and Biopharmaceutics, 2014, 88(1):123-128, Abstract Only (2 pages).
Elkeeb, R. et al., "Transungual Drug Delivery: Current Status," International Journal of Pharmaceutics, 2010, 384:1-8.
English-language machine translation of EP0670159 (A1) issued in U.S. Appl. No. 14/122,025, filed Apr. 1, 2015, 10 pages.
Freiburger Dokumentenserver (FreiDok), Albert-Ludwigs, Unversitat Feiburg im Breisgau, retrieved from the Internet, date accessed: Feb. 5, 2014, 2 pages URL: <http://www.freidok.uni-freiburg.de/volltexte/5682>.
Gayton, J., "Etiology, Prevalence, and Treatment of Dry Eye Disease," Clinical Ophthalmology, 2009, 3:405-412.
Gehlsen et al., "A semifluorinated alkane (F4H5) as novel carrier for cyclosporine A: a promising therapeutic and prophylactic option for topical treatment of dry eye," Graefe's Arch. Clin. Exp. Ophthalmol., (2017) 255(4):767-775.
Gehlsen. U., et al., "Cyclosporine A using F4H5 as liquid drug carrier is effective in treating experimental dry-eye disease," Investigative Ophthalmology & Visual Science, 2015, 56(7):319, Abstract Only (2 pages).
Gerdenitsch, "Emulsions—established and promising drug carriers for parenteral administration," retrieved from Internet, date accessed: Jun. 20, 2016, 2 pages URL: <http:/ipimediaworld.com/wp-content/uploads/2012/05/Pages-from-IPI-Volume-2-Issue-1-11.pdf.>.
Gopal et al., "Use of intravitreal injection of triamcinolone acetonide in the treatment of age-related macular degeneration," Indian J Ophthalmol., 2007, 55(6):431-435, (8 pages).
Griffin, W., "Classification of Surface-Active Agnets by 'HLB'," Journal Of The Society of Cosmetic Chemists, 1949, 1:311-326.
Hardung, H., "Semifluorierte und perfluorierte Vergindungen zur topischen und parenteralen Anwendung," 2008, 188 pages, retrieved from Internet, date accessed: Oct. 10, 2011, URL: <http://www.freidok.uni-freiburg.de/volltexte/5682/pdf/Dissertation_Hardung.pdf>.
Hardung, H., "Semifluorierte und perfluorierte Verbindungen zur topischen und parenteralen Anwendung," 2008, English Language Abstract, 2 pages, retrieved from https://freidok.uni-freiburg.de/data/5682 (retrieved on Jul. 10, 2017).
Hoerauf et al., "Combined Use of Partially Fluorinated Alkanes, Perfluorocarbon Liquids and Silicone Oil: An Experimental Study," Graefe's Archive For Clinical And Experimental Ophthalmology, 2001, 239(5):373-381.
Holm, R. et al., "A novel excipient, 1-perfluorohexyloctane shows limited utility for the oral delivery of poorly water-soluble drugs," European Journal of Pharmaceutical Sciences, 2011, 42: 416-422.
International Preliminary Report on Patentability dated Apr. 23, 2013, for International Patent Application PCT/EP2011/068141, 4 Pages.
International Preliminary Report on Patentability dated Sep. 18, 2012, for International Patent Application PCT/EP2011/053949, 9 Pages.
International Preliminary Report on Patentability dated May 14, 2013, for International Patent Application PCT/EP2011/069795, 8 Pages.
International Preliminary Report on Patentability dated Jul. 10, 2013, for International Patent Application PCT/EP2012/050043, 5 Pages.
International Preliminary Report on Patentability dated Nov. 26, 2013, for International Patent Application PCT/EP2012/059787, 9 Pages.
International Preliminary Report on Patentability dated Nov. 26, 2013, for International Patent Application PCT/EP2012/059788, 8 Pages.
International Preliminary Report on Patentability dated Jul. 29, 2014, for International Application No. PCT/EP2013/051163, 7 pages.
International Preliminary Report on Patentability dated Mar. 17, 2015, for International Application No. PCT/EP2013/068882, 5 pages.
International Preliminary Report on Patentability dated Mar. 17, 2015, for International Application No. PCT/EP2013/068909, 7 pages.
International Preliminary Report on Patentability dated Jan. 26, 2016, for International Application No. PCT/EP2014/065840, 11 pages.
International Preliminary Report on Patentability dated Mar. 26, 2019, for International Application No. PCT/EP2017/073697, 7 pages.
International Preliminary Report on Patentability dated Mar. 26, 2019, for International Application No. PCT/EP2017/074079, 7 pages.
International Search Report for International Application No. PCT/EP2011/053949 dated Sep. 6, 2011, 5 pages.
International Search Report for International Application No. PCT/EP2011/068141 dated Dec. 14, 2011, 2 pages.
International Search Report for International Patent Application PCT/EP2011/069795 dated Jan. 16, 2012, 3 pages.
International Search Report for International Patent Application PCT/EP2012/050043 dated Apr. 24, 2012, 2 pages.
International Search Report for International Application No. PCT/EP2012/059787 dated Dec. 5, 2012, 4 pages.
International Search Report for International Application No. PCT/EP2012/059788 dated Dec. 3, 2012, 4 pages.
International Search Report for International Application No. PCT/EP2013/051163 dated Mar. 4, 2013, 4 pages.
International Search Report for International Application No. PCT/EP2013/068882 dated Oct. 30, 2013, 4 pages.
International Search Report for International Application No. PCT/EP2013/068909 dated Dec. 5, 2013, 4 pages.
International Search Report for International Application No. PCT/EP2014/065840 dated Oct. 7, 2014, 4 pages.
International Search Report for International Application No. PCT/EP2016/073262 dated Nov. 18, 2016, 5 pages.
International Search Report for International Application No. PCT/EP2016/073263 dated Dec. 23, 2016, 3 pages.
International Search Report for International Application No. PCT/EP2017/073697 dated Nov. 6, 2017, 4 pages.
International Search Report for International Application No. PCT/EP2017/074079 dated Dec. 22, 2017, 4 pages.
International Search Report for International Application No. PCT/EP2017/083770 (revised version) dated Jul. 6, 2018, 4 pages.
International Search Report and Written Opinion for International Application No. PCT/EP2017/083770 dated Jul. 6, 2018, 14 pages.
Ishizaki et al., "Treatment of Diabetic Retinopathy," Forum: Complication, Practice, 2009, 26(5): 474-476 (3 pages).
Jonas et al., "Intravitreal triamcinolone acetonide for exudative age-related macular degeneration," Br J Ophthalmol, 2003, 87:462-468.
Joussen et al., "The concept of heavy tamponades—chances and limitations," Graefes Arch Exp Ophthalmol, 2008, 246:1217-1224.
JP 2000511157A, English Machine Translation of the Abstract, Description, and Claims, Espacenet, Date Accessed: Feb. 10, 2016, 15 pages.
JPS6452722, English Machine Translation of the Abstract, Description, and Claims, Espacenet, Date Accessed: Feb. 10, 2016, 4 pages.
Kaercher et al., "NovaTears® as new Therapy in Dry Eye Results from three prospective, multicenter, non-interventional studies in different patient populations," TFOS Conference (Tear Film & Ocular Surface), Sep. 7-10, 2016, Montpellier, France, Poster Session II, Poster No. 60, 1 page.
Knepp et al., "Stability of Nonaqueous Suspension Formulations of Plasma Derived Factor IX and Recombinant Human Alpha Interferon at Elevated Temperatures," Pharmaceutical Research, 1998, 15 (7):1090-1095.

(56) References Cited

OTHER PUBLICATIONS

Kociok, N., "Influence on Membrane-Mediated Cell Activation by Vesicles of Silicone Oil or Perfluorohexyloctane," Graefe's Archive for Clinical and Experimental Ophthalmology, 2005, 243, 345-358.
Lallemand et al., "Cyclosporine A delivery to the eye: a pharmaceutical challenge," European Journal of Pharmaceutics and Biopharmaceutics, 2003, 56(3):307-318, Abstract Only (1 page).
Lemp, M., "Management of Dry Eye Disease," The American Journal of Managed Care, 2008, 14 (3):S88-S101.
Lin, H. et al., "Dry eye disease: A review of diagnostic approaches and treatments," Saudi Journal of Ophthalmology, 2014, 28:173-181.
Mackiewicz, J. et al., "In Vivo Retinal Tolerance of Various Heavy Silicone Oils," Investigative Ophthalmology & Visual Science, 2007, 48 (4):1873-1883.
Matteucci et al., "Biocompatibility assessment of liquid artificial vitreous replacements: relevance of in vitro studies," Survey of Ophthalmology, 2007, 52(3):289-299, Abstract Only (1 page).
Meinert, H. et al., "Semifluorinated Alkanes—A New Class of Compounds with Outstanding Properties for Use in Ophthalmology," European Journal of Ophthalmology, 2000, 10 (3), 189-197.
Meinert, H. et al., "The Use of Semifluorinated Alkanes in Blood-Substitutes," Biomaterials, Artificial Cells, and Immobilization Biotechnology, 1993, 21 (5):583-595.
Messmer, E.M., "The Pathophysiology, Diagnosis, and Treatment of Dry Eye Disease," (2015) Deutsches Arzteblatt International, 112(5):71-82.
Messmer et al., "Semifluorierte Alkane als Therapie bei Meibomdrüsen-Dysfunktion Ergebnisse einer prospektiven, multizentrischen Beobachtungsstudie", Presentation, DOG-Kongress, Sep. 29-Oct. 2, 2016, Berlin DOG (Deutsche Ophtalmologische Gesellschaft), Poster No. PSa03-02, 1 page (German language version).
Messmer et al., "Semifluorinated Alkanes as a Therapy for Meibomian Gland Dysfunction Results of a prospective, multi-centered observational study", Presentation, DOG-Kongress, Sep. 29, 2016-Oct. 2, 2016, Berlin DOG (Deutsche Ophtalmologische Gesellschaft), Poster No. PSa03-02, English Translation, 6 pages.
Messmer et al. "Semifluorinated Alkanes as a Therapy for Meibomian Gland Dysfunction Results of a prospective, multi-centered observational study", Presentation, DOG-Kongress, Sep. 29, 2016-Oct. 2, 2016, Berlin DOG (Deutsche Ophtalmologische Gesellschaft), Ophthalmologe, Aug. 2016 Poster No. PSa03-02, English Translation of Abstract, p. 138.
Murdan, S., "Enhancing the Nail Permeability of Topically Appied Drugs," Expert Opinion on Drug Delivery, 2008, 5 (11):1267-1282.
O'Rourke, M. et al., "Enhancing Delivery of Topical Ocular Drops," Cataract & Refractive Surgery Today Europe, 2016, 2 pages.
Perry, "Dry Eye Disease: Pathophysiology, Classification, and Diagnosis," The American Journal of Managed Care, 2008, 14(3):S79-S87.
Pflugfelder et al., "Treatment of Blepharitis: Recent Clinical Trials," 2014, 12(4):273-284, Abstract Only (2 pages).
Pflugfelder et al., "The Pathophysiology of Dry Eye Disease What We Know and Future Directions for Research," Ophthalmology (2017) 124(11 Supplement): S4-S13.
Pinarci, E. et al., "Intraocular Gas Application in the Diagnosis and Treatment of Valsalva Retiopathy in Case with Premacular Hemorrhage," XP002625604, Retina Vitreus, 2009, 17 (2):153-155, 1 page, abstract only.
Plassmann, M. et al., "Trace Analytical Methods for Semifluorinated n-Alkanes in Snow, Soil, and Air," Analytical Chemistry, 2010, 82(11):4551-4557.
Plassmann, M. et al., "Theoretical and Experimental Simulation of the Fate of Semifluorinated n-Alkanes During Snowmelt," Environmental Science & Technology, 2010, 44(17):6692-6697.
Rosca-Casian, O. et al., "Antifungal Activity of Aloe vera Leaves," Fitoterapia, 2007, 28, 219-222.
Rosenberg, A., "Effects of Protein Aggregates: An Immunologic Perspective," The AAPS Journal, 2006, 8 (3), E501-E507.
Sall, K. et al. "Two Multicenter, Randomized Studies of the Efficacy and Safety of Cyclosporine Ophthalmic Emulsion in Moderate to Severe Dry Eye Disease," Ophthalmology, 2000, 107(4):631-639.
Sato et al., "Vitrectomy and Intraocular Lens Implantation for Cytomegalovirus Retinitis in a Patient with Acquired Immunodeficiency Syndrome," Presented by Medical Online, New Ophthalmology, 1999, 16(7): 995-998 (4 pages).
Schmutz et al., "Fluorinated Vesicles Made from Combinations of Phospholipids and Semifluorinated Alkanes. Direct Experimental Evidence of the Location of the Semifluorinated Alkane within the Bilayer," Langmuir, 2003, 19:4889-4894.
Schnetler et al., "Lipid composition of human meibum: a review," S Afr Optom, 2013, 72(2), 86-93.
Spöler et al., "Towards a New in vitro Model of Dry Eye: The ex vivo Eye Irritation Lest," Developments in Ophthalmology, 2010, 45, 93-107.
Steven, P. et al. "Semifluorinated Alkane Eye Drops for Treatment of Dry Eye Disease—A Prospective, Multicenter Noninterventional Study" Journal of Ocular Pharmacology and Therapeutics, 2015, 31(8):498-503.
Steven et al., "Semifluorinated Alkane Eye Drops for Treatment of Dry Eye Disease Due to Meibomian Gland Disease," Journal of Ocular Pharmacology and Therapeutics, 2017, 33(9):1-8.
Stevenson, C., "Characterization ofProtein and Peptide Stability and Solubility in Non-Aqueous Solvents," Current Pharmaceutical Biotechnology, 2000, 1, 165-182.
Tiffany, J.M., "Individual Variations in Human Meibomian Composition," Exp. Eye Res., 1978, 27, 289-300.
Troiano et al., "Effect of Hypotonic .4% Hyaluronic Acid Drops in Dry Eye Patients: A Cross-Study," Cornea 27(10): 1126-1130, 1 page (Abstract Only).
Wang, W., "Lyophilization and Development of Solid Protein Pharmaceuticals," International Journal of Pharmaceutics, 2000, 203, 1-60.
"What is retinal vitrectomy?" Presented by: Medical Online, Obesity and Diabetes Mellitus, 2005, 4(2): 284-286 (3 pages).
Wong et al., "Perfluorocarbons and Semifluorinated Alkanes," Seminars in Ophthalmology; vol. 15 (1), 2000, p. 25-35.
Wu et al., "Physicochemical characterization and aerosol dispersion performance of organic solution advanced spray-dried cyclosporine A multifunctional particles for dry powder inhalation aerosol delivery," International Journal of Nanomedicine, 2013, 8:1269-1283.
Xalatan, Latanoprost Ophthalmic Solution, 50 µg/mL Prostaglandin $F_{2\alpha}$ analogue, Product Monograph, Jul. 21, 2014, 30 pages.
Zhang et al., "Surface micelles of semifluorinated alkanes in Langmuir-Blodgett monolayers," Phys. Chem. Chem., Phys., 2004, 6:1566-1569.
German, E.J., et al., "Reality of drop size from multi-dose eye drop bottles: is it cause for concern?" Eye, 1999, 13:93-100.
Garritty, James, "Blepharitis-17. Eye Diseases—MSD Manual Professional Edition," 3 pages, (2016); https://www.msdmanuals.com/ja-jp/プロフェッショナル/17- 眼疾患/ 眼瞼および流涙疾患/眼瞼炎.
Bron, A.J. et al., "Grading of Corneal and Conjunctival Staining in the Context of Other Dry Eye Tests," Cornea, 2003, 22(7):640-650.
Matteucci et al., "Biocompatibihty assessment of liquid artificial vitreous replacements: relevance of in vitro studies," Survey of Ophthalmology, 2007, 52(3):289-299.
Nepp, J. et al., "Arbeitsablauf zur Behandlung des Trockenen Auges, ein Versuch der Zuordnung von Diagnose zur Therapie," Spektrum der Augenheilkunde, 2016, 30:122-136.
Pflugfelder et al., "Treatment of Blepharitis: Recent Clinical Trials," 2014, 12(4):273-284.
Schiffman, R.M. et al., "Reliability and Validity of the Ocular Surface Disease Index," Arch. Ophthalmol., 2000, 118(5):615-621.
Shapiro, A et al., "Schirmer Test and Break-Up Time of Tear Film in Normal Subjects," Am J Ophthalmol., 1979, 88(4):752-7.
Benezra et al., "Cyclosporine Eyedrops for the Treatment of Severe Vernal Keratoconjunctivitis," American Journal of Ophthalmology, 1986, 101:278-282.

(56) References Cited

OTHER PUBLICATIONS

Bhargava et al., "Ocular Allergic Disease," Drugs of Today/Medicamentos de Actualidad, J.R. Prous SS.A. International Publishers, 1998, 34(11):957-971.

PHARMACEUTICAL COMPOSITIONS FOR USE IN THE THERAPY OF BLEPHARITIS

CROSS-REFERENCE TO RELATED APPLICATIONS

This application is a U.S. national stage application filed under 35 U.S.C. § 371 of International Application No. PCT/EP2017/073697, filed on Sep. 20, 2017, which claims priority to, and the benefit of, European Application No. 16190138.4, filed Sep. 22, 2016, the contents of each of which are incorporated herein by reference in their entireties.

BACKGROUND OF THE INVENTION

Blepharitis refers to a family of inflammatory disease processes of the eyelid(s). It usually involves the part of the eyelid where the eyelashes grow and affects both eyelids. A number of diseases and conditions can lead to blepharitis, such as bacterial infection, allergies, clogged oil glands or other conditions. The severity can vary and onset can be acute, resolving without treatment within 2 to 4 weeks, but more generally blepharitis is a long-standing chronic inflammation of varying severity.

Blepharitis can be divided anatomically into two sub-indications: Anterior and posterior blepharitis. Anterior blepharitis refers to inflammation mainly centered around the skin, eyelashes and follicles, while the posterior variant involves the meibomian gland orifices, meibomian glands, and tarsal plate. (Pflugfelder et. al, *Ocul. Surf* 2014 October; 12(4):273-84) Anterior blepharitis usually is subdivided further into staphylococcal and seborrheic variants. Frequently, a considerable overlap exists in these processes in individual patients. Blepharitis often is associated with systemic diseases, such as rosacea, atopy and seborrheic dermatitis, as well as ocular diseases, such as dry eye syndromes, chalazion, trichiasis, conjunctivitis, and keratitis.

The pathophysiology of blepharitis frequently involves bacterial colonization of the eyelids. This results in direct microbial invasion of tissues, immune system-mediated damage, or damage caused by the production of bacterial toxins, waste products, and enzymes. Colonization of the lid margin is increased in the presence of seborrheic dermatitis or meibomian gland dysfunction. Patients with blepharitis typically present with symptoms of eye irritation, itching, erythema of the lids, and/or changes in the eyelashes.

Blepharitis is often a chronic condition that is difficult to treat. A systematic and long-term commitment to a program of eyelid margin hygiene usually is the basis for the treatment of blepharitis, which is not a cure but a process to be carried out over prolonged periods of time. Useful medications in the treatment of blepharitis may include medications to fight infection (e.g. by topical antibiotics), to control inflammation (e.g. by topical corticosteroids), to affect the immune system (e.g. by immune suppressants) or by treating the underlying condition. Furthermore, conjunctivitis and keratitis can result as a complication of blepharitis and require additional treatment.

J. Nepp et al. provide in *Spektrum Augenheilkd* (2016) 30:122-136 a workflow-chart for dry eye management from diagnosis to therapy with a compilation of 149 artificial tear medications and application methods. For the treatment of blepharitis and Meibomian gland dysfunction 17 different compound currently available on the market have been compiled under "lubricants—lipids". Among those the compound EvoTears® (Ursa-Pharm Arzneimittel GmbH, Germany) containing perfluorohexyl-octane has been listed.

Nevertheless, in view of the prevalence of blepharitis and the complex interdependencies with other ophthalmic diseases and conditions such as, for example, dry eye disease, there is still a need for further therapeutic options that allow to directly and efficiently address specific forms or sub-indications of blepharitis with high efficacy. It is therefore an object of the present invention to provide pharmaceutical compositions that allow the treatment of specific forms of blepharitis with high efficacy and a minimized probability of adverse side-effects or interdependencies with other conditions or medications.

SUMMARY OF THE INVENTION

In a first aspect, the present invention relates to a pharmaceutical composition comprising or essentially consisting of 1-perfluorohexyl-octane (F6H8) for use in the therapy, treatment, prevention or amelioration of anterior or posterior blepharitis or symptoms associated therewith. In a preferred embodiment, the present invention provides a pharmaceutical composition comprising 1-perfluorohexyl-octane (F6H8) for use in the therapy, treatment, prevention or amelioration of posterior blepharitis or symptoms associated therewith. In a particularly preferred embodiment, the present invention provides a pharmaceutical composition consisting of 1-perfluorohexyl-octane (F6H8) for use in the therapy, treatment, prevention or amelioration of posterior blepharitis or symptoms associated therewith.

In a second aspect, the present invention relates to a method of treating a patient suffering from anterior or posterior blepharitis or symptoms associated therewith, comprising topically administering a pharmaceutical composition comprising or essentially consisting of 1-perfluorohexyl-octane to the eye of that patient.

In a third aspect, the present invention relates to the use of a pharmaceutical composition comprising or essentially consisting of 1-perfluorohexyl-octane for the therapy, treatment, prevention or amelioration of anterior or posterior blepharitis or symptoms associated therewith.

In a fourth aspect, the present invention provides a pharmaceutical kit for the therapy, treatment, prevention or amelioration of anterior or posterior blepharitis or symptoms associated therewith, comprising
  a) a pharmaceutical composition for use according to the first aspect of the invention comprising or essentially consisting of 1-perfluorohexyl-octane;
  b) a container for holding the composition, wherein said container comprises a dispensing means adapted for topical administration of the composition to an eye surface, into a lower eyelid, to the lacrimal sac or to an ophthalmic tissue; and
  c) directions for use of the composition in the therapy, treatment, prevention or amelioration of anterior or posterior blepharitis, preferably posterior blepharitis or symptoms associated therewith.

DETAILED DESCRIPTION OF THE INVENTION

In a first aspect, the present invention relates to a pharmaceutical composition comprising 1-perfluorohexyl-octane (F6H8) for use in the therapy, treatment, prevention or amelioration of anterior or posterior blepharitis or symptoms associated therewith. In a particularly preferred embodiment, the present invention provides a pharmaceutical composition consisting of 1-perfluorohexyl-octane (F6H8) for use in the therapy, treatment, prevention or amelioration of posterior blepharitis or symptoms associated therewith. According to the present invention, the clinical condition to be treated in a patient diagnosed therewith or to be prevented by therapy may be either anterior or posterior blepharitis, which are specific sub-indications of blepharitis as the more general indication. The anterior or posterior blepharitis to be treated according to the present invention may be acute or chronic and may or may not yet be manifested in the case of the prevention of a suspected anterior or posterior blepharitis.

The term therapy, treatment, prevention or amelioration as used herein, may be summarized by the term "treatment" and means, as used herein, in a broad sense any act performed on a patient useful in the management or prevention of a medical condition or disease of such patient.

The term anterior blepharitis as used herein refers to an inflammation mainly centered around the skin, eyelashes, and follicles of an eye or both eyes of a patient mainly affecting the outside front of the eyelid where eyelashes are attached. Anterior blepharitis as used herein further may be subdivided into staphylococcal and seborrheic variants. However, a considerable overlap may exist with respect to the named variants and processes in individual patients frequently.

The term posterior blepharitis as used herein refers to a variant or sub-indication of blepharitis that involves the meibomian gland orifices, the meibomian glands, and the tarsal plate. Posterior blepharitis affects the inner edge of the eyelid that touches the eyeball. Frequently, it is linked to dysfunction of meibomian glands within the eyelids that secrete oils to help lubricate the eye, which creates a favorable environment for bacterial growth. Posterior blepharitis can also develop as a result of other skin conditions, such as acne rosacea and scalp dandruff.

Both variants of blepharitis as referred to herein may or may not be associated with systemic diseases, such as, for example, rosacea, atopy, and seborrheic dermatitis, as well as ocular diseases, such as, for example, dry eye syndromes, chalazion, trichiasis, conjunctivitis, and keratitis.

Furthermore, anterior or posterior blepharitis as referred to herein may or may not involve bacterial colonization of the eyelids and, as a result thereof, may involve direct microbial invasion of tissues, immune system-mediated damage, or damage caused by the production of bacterial toxins, waste products, and enzymes. Furthermore, colonization of the lid margin associated with anterior or posterior blepharitis as referred to herein may or may not be increased in the presence of seborrheic dermatitis or meibomian gland dysfunction. Furthermore, anterior or posterior blepharitis as referred to herein may typically occur together with symptoms of eye irritation, such as, for example, itching, erythema of the lids, and/or changes in the eyelashes.

In a preferred embodiment, however, the present invention relates to a pharmaceutical composition for use in the therapy, treatment, prevention or amelioration of anterior or posterior blepharitis or symptoms associated therewith, wherein the anterior or posterior blepharitis is a posterior blepharitis. Accordingly, the present invention relates to a pharmaceutical composition for use in the therapy, treatment, prevention or amelioration of posterior blepharitis or symptoms associated therewith.

In a further embodiment, the present invention relates to a pharmaceutical composition for use in the therapy, treatment, prevention or amelioration of anterior or posterior blepharitis or symptoms associated therewith, preferably posterior blepharitis, which may occur at certain levels of intensity. For example, the anterior or posterior blepharitis according to the present invention may occur with weak or light intensity or with an average intensity or with a severe intensity (i.e. an intensity above the average intensity) when compared with the distribution of intensities occurring in a group with a representative number of cases of blepharitis.

Accordingly, in one embodiment the present invention relates to a pharmaceutical composition for use in the therapy, treatment, prevention or amelioration of anterior or posterior blepharitis or symptoms associated therewith, wherein the anterior or posterior blepharitis is a severe anterior or posterior blepharitis. In a preferred embodiment, however, the present invention relates to a pharmaceutical composition for use in the therapy, treatment, prevention or amelioration of severe posterior blepharitis, that means posterior blepharitis with severe intensity, or symptoms associated therewith. Surprisingly, it has been found, that the use of the pharmaceutical compositions according to this first aspect of the invention is especially beneficial for the treatment of severe forms of blepharitis as shown by experimental data outlined further below.

The pharmaceutical composition for use in the therapy, treatment, prevention or amelioration of anterior or posterior blepharitis, preferably posterior blepharitis, or symptoms associated therewith comprises 1-perfluorohexyl-octane. 1-perfluorohexyl-octane is also known as F6H8, according to the nomenclature FnHm, wherein n is an integer representing the number of carbon atoms of the linear, unbranched perfluorinated segment and m is an integer representing the number of carbon atoms of the linear, unbranched hydrocarbon segment.

The pharmaceutical composition for use according to the present invention usually comprises 1-perfluorohexyl-octane in an amount of at least 90 wt.-%, preferably in an amount of from 95 to 100 wt.-%, more preferably in an amount of 97 to 99.95 wt.-% and even more preferred in an amount of from 98.5 to 99.9 wt.-% based on the final dosage form. Accordingly, in a preferred embodiment of the present invention the pharmaceutical composition for use in the therapy, treatment, prevention or amelioration of anterior or posterior blepharitis, preferably posterior blepharitis essentially consists of 1-perfluorohexyl-octane. In a specific embodiment, of the present invention the pharmaceutical composition for use in the therapy, treatment, prevention or amelioration of anterior or posterior blepharitis, preferably posterior blepharitis consists of 1-perfluorohexyl-octane. In this particular case the pharmaceutical compositions for use according to the present invention may, as an alternative, be referred to as "pharmaceutical preparation" or "medicinal product". The pharmaceutical composition for use according to the present invention is usually provided as a clear solution, preferably in sterilized form.

In a further preferred embodiment, the pharmaceutical compositions for use according to the present invention are substantially free of a dissolved pharmacological active ingredient which is not 1-perfluorohexyl-octane. As used herein, the term "pharmacological active ingredient" refers to any type of pharmaceutically active compound or drug, i.e. one that produces a pharmacological effect and that may accordingly be useful in the prevention, diagnosis, stabilization, treatment, or generally speaking, the management of a condition or disease. Although free of (other) pharmacologically active ingredients the pharmaceutical compounds for use according to the present invention, however have beneficial therapeutic effects in the treatment or prevention of anterior or posterior blepharitis.

Furthermore, the pharmaceutical composition for use according to the present invention, however may or may not comprise small amounts of 2-perfluorohexyl-octane, which, depending on the source or preparation method may or may not be present in an amount of usually up to 3 wt.-%, preferably in an amount from 0.1 to 2.0 wt.-%, more preferably in an amount of 0.1 to 1 wt.-% of the final dosage form.

In one preferred embodiment, the pharmaceutical compositions for use according to the present invention are substantially free of water and/or substantially free of a preservative. As understood herein, the term 'substantially free' in reference to a composition constituent refers to the presence of said constituent in no more than trace amounts and that if present in trace amounts the constituent provides no technical contribution to the composition.

The pharmaceutical compositions for use according to the present invention are commercially available and may be purchased under the tradename NovaTears® (Novaliq GmbH, Germany) or EvoTears® (URSAPHARM Arzneimittel GmbH, Germany).

The pharmaceutical composition for use according to the present invention may be topically administered to a surface of the eye, into a lower eyelid, to the lacrimal sac or to an ophthalmic tissue of a patient in need thereof. Usually, single droplets of the pharmaceutical composition, preferably single droplets of NovaTears®, are administered directly to the surface of the eye. Preferably, the droplets may be administered into a pocket of the eyelid that may be formed by gently pulling down the lower eyelid of an eye.

The droplets of the pharmaceutical composition, especially the droplets of the pharmaceutical composition consisting essentially of 1-perfluorohexyl-octane usually have a volume of about 8 to 15 µL, often a volume of about 10 µl per droplet. In most cases the present pharmaceutical compositions are administered in an amount of 1 to 6 droplets, preferably 3 to 4 droplets to each eye per day corresponding to a daily overall volume of the pharmaceutical composition of 30 to 40 µl per eye. Usually, the pharmaceutical is administered at a dose of 1 droplet per eye per administration with 3 to 4 administrations per day. Depending on the intensity as well as other factors, such as, for example, associated other diseases as described above, however, modes and volumes of administration as well as the duration of the treatment can vary significantly.

In yet another embodiment of the pharmaceutical composition for use according to the present invention, the anterior or posterior blepharitis may be associated with an underlying clinical condition selected from the group consisting of bacterial infections, seborrheic dermatitis, clogged or malfunctioning oil glands in the eyelids, rosacea, allergic reactions and infestation with eyelash mites and/or lice. Allergic reactions may be caused by or attributed to for example, eye medications, to contact lens solutions or to certain eye makeup.

In yet another embodiment, the pharmaceutical composition for use according to the present invention, the anterior or posterior blepharitis, preferably the posterior blepharitis to be treated, prevented or ameliorated is associated with myobomian gland dysfunction and/or dry eye disease (DED).

In a further embodiment, the pharmaceutical composition for use according to the present invention is not administered to patients wearing contact lenses.

In a further embodiment, it has been found advantageous that the pharmaceutical composition for use in the therapy, treatment, prevention or amelioration of anterior or posterior blepharitis, preferably posterior blepharitis, or symptoms associated therewith, the pharmaceutical composition is administered to a patient having a Tear Film Break-Up Time (TFBUT; Shapiro A., et. al. Am J Ophthalmol. 1979 October; 88(4):752-7) of up to 10 s, preferably of up to 6 s. (Shapiro A., et. al. Am J Ophthalmol. 1979 October; 88(4): 752-7).

Furthermore, it has been found advantageous that the pharmaceutical composition for use according to the present invention is administered to a patient having an Ocular Surface Disease Index in the range of from 16 to 55 (Schiffman, R. M., et. al, Arch. Ophthalmol. 118:615-621, 2000).

In yet another embodiment, it has been found advantageous that the pharmaceutical composition for use according to the present invention is administered to a patient having a Schirmer I Test value (Shapiro A., et. al. Am J Ophthalmol. 1979 October; 88(4):752-7) of at least 2 mm (2 mm and above), preferably 5 mm and above as recorded during a 5 min test period.

Furthermore, it has been found advantageous that the pharmaceutical composition for use according to the present invention is administered to a patient having an added peripheral corneal and conjunctival Oxford staining grade of up to 10. (Bron, A. J., et. al., Cornea. 22:640-650, 2003.)

Preferably, in yet another embodiment, it has been found advantageous that the pharmaceutical composition for use according to the present invention is administered to a patient having a Tear Film Break-Up Time of up to 10 s, an Ocular Surface Disease Index in the range of from 16 to 55, a Schirmer I Test value of at least 2 mm, and an added peripheral corneal and conjunctival Oxford staining grade of up to 10.

In a further aspect, the present invention as described in detail above relates to a method of treating a patient suffering from anterior or posterior blepharitis or symptoms associated therewith, comprising topically administering a pharmaceutical composition comprising or essentially consisting of 1-perfluorohexyl-octane to the eye of that patient. In a specific embodiment, the method comprises topically administering a pharmaceutical composition consisting of 1-perfluorohexyl-octane to the eye of that patient. In this aspect also, the treatment of posterior blepharitis is preferred according to all embodiments outlined above for the first aspect of the invention.

In yet another aspect, the present invention relates to the use of a pharmaceutical composition as described in detail above comprising or essentially consisting of 1-perfluorohexyl-octane for the therapy, treatment, prevention or amelioration of anterior or posterior blepharitis or symptoms associated therewith. In specific embodiment, the present invention relates to the use of a pharmaceutical composition consisting of 1-perfluorohexyl-octane for the therapy, treatment, prevention or amelioration of anterior or posterior blepharitis or symptoms associated therewith. Likewise, in this aspect of the invention the treatment of posterior blepharitis is preferred in accordance with all embodiment outlined above for the first aspect of the invention.

In another aspect, the present invention relates to a pharmaceutical kit for the therapy, treatment, prevention or amelioration of anterior or posterior blepharitis or symptoms associated therewith, comprising
 a) a pharmaceutical composition for use according to the first aspect of the invention comprising or essentially consisting of 1-perfluorohexyl-octane;
 b) a container for holding the composition, wherein said container comprises a dispensing means adapted for topical administration of the composition to an eye surface, into a lower eyelid, to the lacrimal sac or to an ophthalmic tissue, and c) directions for use of the composition in the therapy, treatment, prevention or amelioration of anterior or posterior blepharitis, preferably posterior blepharitis or symptoms associated therewith.

According to item a) of this aspect of the invention the pharmaceutical kit comprises a pharmaceutical composition for use as described above for the first aspect of the present invention. In a specific embodiment, in item a) the pharmaceutical composition is a pharmaceutical composition for use according to the first aspect of the invention consisting of 1-perfluorohexyl-octane.

A container as used in connection with item b) of this aspect of the invention can be provided in any suitable form as a container for single use holding a single dose of the pharmaceutical composition or as a container for multiple uses holding a plurality of single doses. Preferably, the container comprises a dispensing means which allows for dropwise topical administration of the pharmaceutical composition to a surface of the eye of a patient. In one embodiment, the container comprising a dispensing means may be a conventional dropper bottle such as a bottle made of glass or a thermoplastic elastomer with a suitable dispensing means or single-use droppers.

In a further preferred embodiment of this aspect of the invention, the dispensing means comprises a dropper of dimensions such as to dispense droplets having a volume of about 8 to 15 µL, preferably of about 10 µl. With a small droplet volume, precise dosing to the eye can be achieved and an excess amount of discharge of a substantial fraction of the composition from the eye subsequent to administration can be avoided.

Directions for use of the pharmaceutical composition according to item c) of this aspect of the invention can be provided in any suitable form such as, for example, as an enclosed label or instruction leaflet in printed or other readable form.

Alternatively, the directions for use can be provided in electronic or computer readable form, such as a barcode or a QR-code.

The following examples serve to illustrate the invention however these are not to be understood as restricting the scope of the invention.

EXAMPLES

A prospective, uncontrolled, open-label, multi-center observational study was conducted with a total of 72 (53 female, 19 male) patients included, with 1 to 20 patients per site. Two patients were lost for follow-up during the study. Patients to be included had to fulfill following criteria:

Males or females≥18 years of age;
Patients with symptoms as determined by
Tear Film Break-Up Time (TFBUT)≤10 s
Ocular Surface Disease Index≥16 and ≤55
Schirmer I Test≥2 mm (recorded within 5 min)
Sum of peripheral corneal and conjunctival staining grade≤10 (Oxford)
Altered secretion and expressibility of the meibomian glands.

Among those, patients fulfilling the following criteria were not included in the study:

Known hypersensitivity to any of the components of NovaTears®;
Contact lens wear, pregnancy, or breast feeding;
Presence of dry eye disease (DED) caused by any other known underlying systemic disease;
Planned ophthalmologic surgical procedure during the course of the study;
Use of lipid-containing or tear-film stabilizing eye drops/sprays except cyclosporin formulations.

Patients selected as described above were administered 1-perfluorohexyloctane (F6H8) eye drops, manufactured under the tradename "NovaTears®" (Novaliq GmbH, Heidelberg, Germany) for a period of 7 weeks. Said formulation consists essentially of 1-perfluorohexyloctane (F6H8), it is water-free and contains no additional preservatives or ingredients. A dose of 3 to 4 droplets (corresponding to to 40 µl, 10 µl per drop) per eye and day were administered topically to the eye, with 1 droplet being administered as a single dose. NovaTears® single droplets were administered directly to the surface of the eye into a pocket that was formed by gently pulling down the lower eyelid. Assessment of the eyes treated was performed once before the start of NovaTears® administration (baseline) and once after 7 weeks of treatment (follow-up).

Assessment of Blepharitis

Anterior blepharitis involves inflammation of the lid margin anterior to the gray line and is usually concentrated around the eyelashes and follicles. Posterior blepharitis involves inflammation of the posterior lid margin. The severity of anterior and posterior blepharitis was rated separately for each eye by selecting one of the following ratings: "none", "+", "++", "+++" (with "+++" indicating most severe blepharitis anterior or posterior).

Assessment of Anterior Blepharitis

Table I summarizes the assessment of 122 eyes from 61 patients, with the results of right and left eyes combined. Herein, the evaluation of anterior blepharitis showed that patients clearly profit from the treatment with 1-perfluorohexyloctane (F6H8). The severity of blepharitis was observed to be decreased for all patients, including patients with blepharitis severity scores indicated as "++" and "+".

TABLE I

| Assessment of anterior blepharitis | | | | |
|---|---|---|---|---|
| Grade | none | + | ++ | +++ |
| Baseline | 48 | 59 | 15 | 0 |
| Follow-up | 73 | 42 | 7 | 0 |

Assessment of Posterior Blepharitis

Table II summarizes the assessment of 122 eyes from 61 patients, with the results of right and left eyes combined. Herein, the assessment of posterior blepharitis showed that the severity of blepharitis was observed to be decreased for all patients after treatment with 1-perfluorohexyloctane, including patients with blepharitis severity scores rated as "++" and "+". The most significant reduction in the severity of posterior blepharitis after treatment with 1-perfluorohexyloctane (F6H8), however, was found in patients with the most severe posterior blepharitis rated as "+++".

TABLE II

| Assessment of posterior blepharitis | | | | |
|---|---|---|---|---|
| Grade | none | + | ++ | +++ |
| Baseline | 31 | 53 | 32 | 6 |
| Follow-up | 60 | 51 | 11 | 0 |

The observed changes in severity of anterior and posterior blepharitis between baseline and follow-up for both eyes combined are shown in Table III and Table IV (total sample size=122 eyes (61 patients)). A Wilcoxon Rank Sum test (n=61 each) showed significant changes to the severity score both for anterior blepharitis (right eye: p=0.0040; left eye: p=0.020) and posterior blepharitis (right eye and left eye: p<0.0001).

TABLE III

Assessment of anterior blepharitis (sum scores of severity ratings), changes from baseline for both eyes - shift table

| Baseline | Follow-up | | | |
|---|---|---|---|---|
| | none | + | ++ | +++ |
| none | 31 | 15 | 2 | 0 |
| + | 38 | 20 | 1 | 0 |
| ++ | 4 | 7 | 4 | 0 |
| +++ | 0 | 0 | 0 | 0 |

TABLE IV

Assessment of posterior blepharitis (sum scores of severity ratings), changes from baseline for both eyes - shift table

| Baseline | Follow-up | | | |
|---|---|---|---|---|
| | 0 (none) | + | ++ | +++ |
| 0 (none) | 26 | 5 | 0 | 0 |
| + | 20 | 30 | 3 | 0 |
| ++ | 10 | 14 | 8 | 0 |
| +++ | 4 | 2 | 0 | 0 |

Lid Margin Assessment

As a further parameter abnormal lid margin features, such as teleangiectasia, plugging and lid swelling were assessed in the study. Assessment was performed for each eye separately. As summarized in Table V lid margin assessment revealed that all abnormal lid margin features such as teleangiectasia, plugging and lid swelling were significantly reduced after treatment with 1-perfluorohexyloctane (F6H8).

TABLE V

Assessment of lid margin

| | Teleangiectasia | Plugging | Lid Swelling |
|---|---|---|---|
| Baseline | 74 | 90 | 30 |
| Follow-up | 49 | 59 | 20 |

The invention claimed is:

1. A method of treating anterior blepharitis, in a patient in need thereof, comprising administering to the patient a pharmaceutical composition consisting of 1-perfluorohexyloctane (F6H8), and wherein the patient is characterized as having
    (i) a Tear Film Break-Up Time (TFBUT) of up to 10 s,
    (ii) an Ocular Surface Disease Index in the range of from 16 to 55,
    (iii) a Schirmer I Test value of at least 2 mm recorded within 5 min, and
    (iv) an added peripheral corneal and conjunctival Oxford staining grade of up to 10.

2. The method according to claim 1, wherein the anterior blepharitis is a severe anterior blepharitis.

3. The method according to claim 1, wherein said composition is topically administered to a surface of the eye, into a lower eyelid, to the lacrimal sac or to an ophthalmic tissue of the patient.

4. The method according to claim 3, wherein said composition is administered in an amount of 1 to 6 droplets to each eye per day.

5. The method according to claim 1, wherein the anterior blepharitis is associated with an underlying clinical condition selected from the group consisting of bacterial infections, seborrheic dermatitis, rosacea, allergic reactions and infestation with eyelash mites and/or lice.

6. The method according to claim 1, wherein the anterior blepharitis is mainly centered around the skin, eyelashes, and follicles of an eye or both eyes of a patient.

7. The method according to claim 6, wherein the anterior blepharitis relates to an inflammation affecting the outside front of the eyelid where eyelashes are attached.

8. The method according to claim 6, wherein the anterior blepharitis is selected from staphylococcal and seborrheic blepharitis.

9. The method according to claim 4, wherein the pharmaceutical composition is administered in an amount of 3 to 4 droplets to each eye per day.

10. The method according to claim 1, wherein the pharmaceutical composition is administered in an amount of 3 to 4 droplets at a daily overall volume of 30 to 40 µl to each eye per day.

11. The method according to claim 1, wherein the pharmaceutical composition is administered as single droplets of 8 to 15 µl or as single droplets of 10 µl volume.

12. The method according to claim 1, wherein the pharmaceutical composition is administered at a dose of 1 droplet per eye with 3 to 4 administration per day.

\* \* \* \* \*

UNITED STATES PATENT AND TRADEMARK OFFICE
CERTIFICATE OF CORRECTION

PATENT NO. : 11,684,589 B2
APPLICATION NO. : 16/336018
DATED : June 27, 2023
INVENTOR(S) : Günther et al.

It is certified that error appears in the above-identified patent and that said Letters Patent is hereby corrected as shown below:

In the Specification

Column 7, Line 52, "females‡18 years of age" should be "females $\geq$ 18 years of age"

Column 7, Line 54, "(TFBUT)£10 s" should be "(TFBUT) $\leq$ 10 s"

Column 7, Line 55, "index‡16 and £55" should be "index $\geq$ 16 and $\leq$ 55"

Column 7, Line 56, "Schirmer I test‡2 mm" should be "Schirmer I test $\geq$ 2 mm"

Column 7, Lines 58, "grade£10 (Oxford)" should be "$\leq$ grade 10 (Oxford)"

Column 8, Line 12, "corresponding to to 40 µl" should be "corresponding to 30 to 40 µl"

Signed and Sealed this
Fourteenth Day of November, 2023

Katherine Kelly Vidal
*Director of the United States Patent and Trademark Office*